(12) United States Patent
Ohnishi et al.

(10) Patent No.: US 7,950,385 B2
(45) Date of Patent: May 31, 2011

(54) DISPOSABLE WARMER AND BAG MEMBER FOR THE SAME

(75) Inventors: Kaori Ohnishi, Matsuyama (JP);
Katsumi Hori, Matsuyama (JP)

(73) Assignee: Nitto Lifetec Corporation, Matsuyama-shi (JP)

( * ) Notice: Subject to any disclaimer, the term of this patent is extended or adjusted under 35 U.S.C. 154(b) by 375 days.

(21) Appl. No.: 12/153,414

(22) Filed: May 19, 2008

(65) Prior Publication Data

US 2008/0289616 A1   Nov. 27, 2008

(30) Foreign Application Priority Data

May 21, 2007   (JP) .................................. 2007-134783

(51) Int. Cl.
*F24J 1/00*   (2006.01)

(52) U.S. Cl. ............. 126/263.01; 126/263.02; 126/204; 607/114

(58) Field of Classification Search .................. 126/204, 126/263.01, 263.02; 607/114
See application file for complete search history.

(56) References Cited

U.S. PATENT DOCUMENTS

| | | | | |
|---|---|---|---|---|
| 3,328,505 | A * | 6/1967 | Spencer | 264/321 |
| 4,294,240 | A * | 10/1981 | Thill | 602/21 |
| 4,516,572 | A * | 5/1985 | Schlein | 602/3 |
| 4,756,299 | A * | 7/1988 | Podella | 126/263.02 |
| 5,722,482 | A * | 3/1998 | Buckley | 165/10 |
| 5,925,010 | A * | 7/1999 | Caprio, Jr. | 602/62 |
| 6,004,662 | A * | 12/1999 | Buckley | 428/304.4 |
| 6,183,855 | B1 * | 2/2001 | Buckley | 428/317.9 |
| 6,227,383 | B1 * | 5/2001 | De Ruiter et al. | 210/504 |
| 6,319,599 | B1 * | 11/2001 | Buckley | 428/308.4 |
| 6,464,672 | B1 * | 10/2002 | Buckley | 604/304 |
| 6,503,855 | B1 * | 1/2003 | Menzies et al. | 442/328 |

(Continued)

FOREIGN PATENT DOCUMENTS

| | | |
|---|---|---|
| EP | 1774934 | 4/2007 |
| EP | 1782767 | 5/2007 |
| JP | 10-314208 | 12/1998 |

(Continued)

OTHER PUBLICATIONS

European Seaarch Report dated Sep. 5, 2008, issued on the corresponding European Application. No. 08009298.4.

*Primary Examiner* — Kenneth B Rinehart
*Assistant Examiner* — Jorge Pereiro
(74) *Attorney, Agent, or Firm* — Edwards Angell Palmer & Dodge LLP (57) ABSTRACT

A disposable warmer of the present invention has a bag including a bag member (A) and a bag member (B); a heater; a heat-sealed portion where the bag member (A) and the bag member (B) are heat-sealed; and a portion with the heater sealed therein. The bag members (A) and (B) are heat-sealed with each other to form the bag, the bag member (A) includes at least a layered structure with a porous film and a nonwoven fabric layer, and the bag member (B) includes at least another layered structure with a stretchable film and another nonwoven fabric layer. The disposable warmer comprises two or more of the portions with the heaters sealed therein independently, and a slit in at least the porous film constituting the bag member (A) of the bag members (A) and (B) in at least one region between the adjacent portions with the heaters sealed therein.

14 Claims, 6 Drawing Sheets

U.S. PATENT DOCUMENTS

| | | | |
|---|---|---|---|
| 6,855,410 B2 * | 2/2005 | Buckley | 428/311.11 |
| 7,036,503 B2 * | 5/2006 | Miyazawa et al. | 128/201.13 |
| 7,419,677 B2 * | 9/2008 | Gueret | 424/400 |
| 7,615,024 B2 * | 11/2009 | Chiang et al. | 602/5 |
| 2002/0142027 A1 * | 10/2002 | Gueret | 424/443 |
| 2002/0164473 A1 * | 11/2002 | Buckley | 428/308.4 |
| 2002/0164474 A1 * | 11/2002 | Buckley | 428/308.4 |
| 2004/0042965 A1 * | 3/2004 | Usui et al. | 424/40 |
| 2005/0145250 A1 * | 7/2005 | Miyazawa et al. | 128/205.25 |
| 2007/0077393 A1 * | 4/2007 | Chiang et al. | 428/131 |
| 2007/0277806 A1 * | 12/2007 | Dodo | 126/263.02 |
| 2008/0206549 A1 * | 8/2008 | Dodo | 428/320.2 |
| 2008/0251062 A1 * | 10/2008 | Dodo | 126/263.02 |
| 2008/0257333 A1 * | 10/2008 | Dodo et al. | 126/263.09 |

FOREIGN PATENT DOCUMENTS

| | | |
|---|---|---|
| JP | 10-328224 | 12/1998 |
| JP | 2000-042021 | 2/2000 |
| JP | 2000-126217 | 5/2000 |
| JP | 2000-288008 | 10/2000 |
| JP | 2001-260293 | 9/2001 |
| JP | 2002-036471 | 2/2002 |
| JP | 2002-085442 | 3/2002 |
| JP | 2002-113819 | 4/2002 |
| JP | 2002-127316 | 5/2002 |
| JP | 2006213385 A * | 8/2006 |
| WO | WO-2006/006657 | 1/2006 |

* cited by examiner

CROSS-PORTIONAL VIEW (FIG. 10A)

TOP VIEW (FIG. 10B)

DISPOSABLE WARMER AND BAG MEMBER FOR THE SAME

BACKGROUND OF THE INVENTION

1. Field of the Invention

The present invention relates to disposable warmers such as disposable body warmers and disposable pocket warmers, and bag members for the disposable warmers. More specifically, it relates to disposable warmers having dramatically improved stretchability as compared to known equivalents; and bag members for the same.

2. Description of the Related Art

Disposable warmers of the type in which their bag is provided with an adhesive layer on one side thereof and which are attachable to any desired portion of the body (adhesive-patch body warmers) have been widely used without distinction of season, typically to warm easily and conveniently in winter and to prevent poor circulation and excessive sensitivity to cold in cooled environment in summer (refer typically to Japanese Unexamined Patent Application Publication (JP-A) No. Hei 10-314208; JP-A No. Hei 10-328224; JP-A No. 2000-42021; JP-A No. 2000-126217; JP-A No. 2000-288008; JP-A No. 2001-260293; JP-A No. 2002-36471; JP-A No. 2002-85442; JP-A No. 2002-113819; and JP-A No. 2002-127316). Such adhesive-patch disposable warmers are used as being applied typically to clothes such as socks, hose, and underclothes; footwear such as shoes and boots; and skin.

Figure 13:
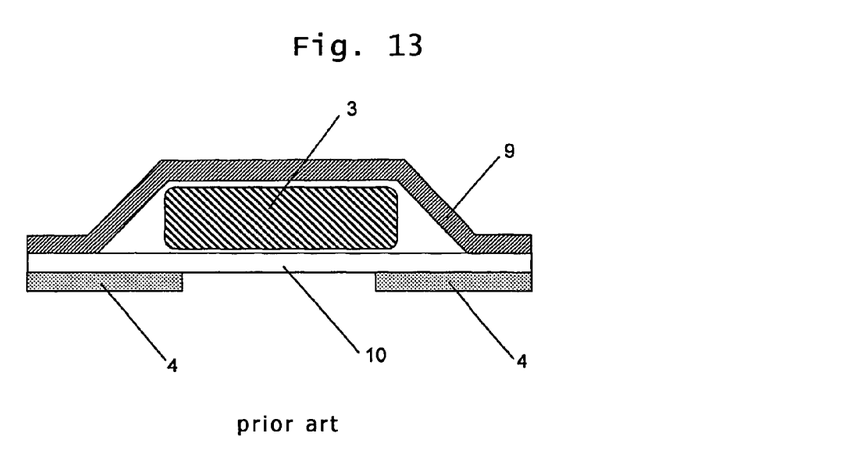
FIG. 13 is a schematic cross-portional view illustrating a known adhesive-patch disposable warmer.

Known general disposable warmers have, for example, a structure as shown in FIG. 13. Specifically, this structure includes two bag members (a bag member 9 and a bag member 10), i.e., a top member and a back member, in which the two members are heat-sealed with a heat sealing device to form a bag, and a heater 3 mainly including, for example, iron powder is sealed in the bag. The bag member is provided with a pressure-sensitive adhesive layer 4 to be attached to an adherend. Examples of the bag member include (1) a multi-layer member as a layered material of an air-permeable porous base film and a nonwoven fabric layer; and (2) a multilayer member as a layered material of a heat-sealable airtight base film and a nonwoven fabric layer.

However, base films used in bag members of the disposable warmers generally have poor stretchability, whereby the known disposable warmers have poor stretchability and unsatisfactory wearing comfort. With increasing requirements therefor, disposable warmers should have high stretchability so as to attach easily and conveniently and to wear comfortably.

Figure 14:
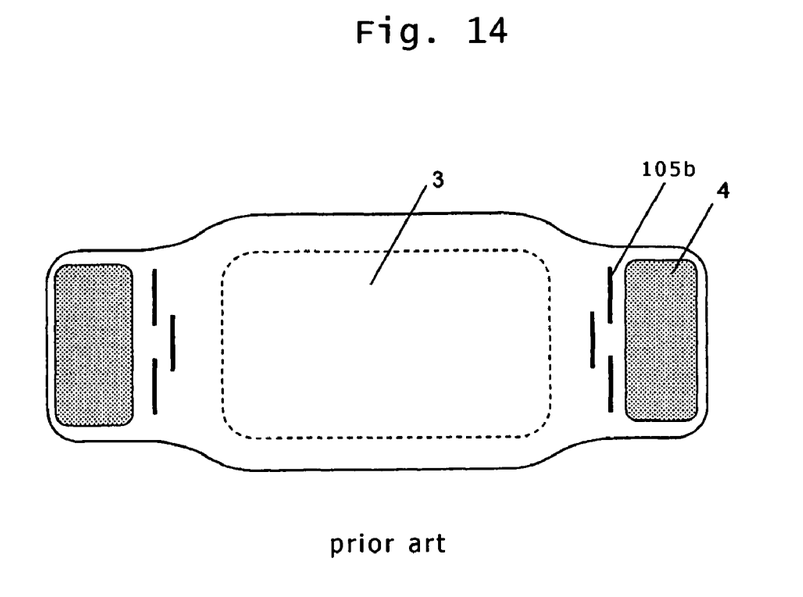
FIG. 14 is a schematic explanatory view, seen from bottom (side facing an adherend), of a known adhesive-patch disposable warmer with slits.

To solve these problems, there is known a technique of providing slits 105b (cuts or notches) at edges of a disposable warmer, which slits 5b pierce the warmer in a thickness direction, as illustrated in FIG. 14. This technique provides a disposable warmer that extensionally deforms to some extent. However, the warmer is stretchable only to such an extent that the slits deform and thereby still has insufficient stretchability. In other words, this technique fails to provide a sufficiently stretchable body warmer. In contrast, a disposable warmer, if provided with relatively large piercing slits, has poor strength.

SUMMARY OF THE INVENTION

An object of the present invention is to provide a disposable warmer having dramatically improved stretchability while maintaining its strength, as compared to known disposable warmers. Another object of the present invention is to provide a bag member for use in the disposable warmer.

After intensive investigations, the present inventors found that a disposable warmer having dramatically improved stretchability while maintaining its strength is obtained by forming a bag with two types of bag members, i.e., a layered material of a porous film and a nonwoven fabric, and another layered material of a stretchable film and a nonwoven fabric; providing two or more of portions with heaters sealed therein; and slitting at least the porous film of the bag member composed of the layered material of the porous film and the nonwoven fabric in a region between the portions with heaters sealed therein. In addition, they found that a disposable warmer having further improved performance is obtained by providing a heater-free portion between the portions with heaters sealed therein; and slitting only the porous film of the bag member composed of the layered material of the porous film and the nonwoven fabric in the heater-free portion. The present invention has been made based on these findings.

Specifically, a disposable warmer of the present invention has a bag including a bag member (A) and a bag member (B); a heater; a heat-sealed portion where the bag member (A) and the bag member (B) are heat-sealed; and a portion with the heater sealed therein. The bag members (A) and (B) are heat-sealed with each other to form the bag, the bag member (A) includes at least a layered structure with a porous film and a nonwoven fabric layer, and the bag member (B) includes at least another layered structure with a stretchable film and another nonwoven fabric layer. The disposable warmer comprises two or more of the portions with the heaters sealed therein independently, and a slit in at least the porous film constituting the bag member (A) of the bag members (A) and (B) in at least one region between the adjacent portions with the heaters sealed therein.

Preferably, the disposable warmer further comprises a heater-free portion in at least the one region between the adjacent portions with the heaters sealed therein. The heater-free portion is not heat-sealed and includes no heater, and a slit may be arranged, of the bag members (A) and (B) in at least the porous film constituting the bag member (A) at the heater-free portion.

Preferably, of the bag members (A) and (B), a slit is arranged only in the porous film constituting the bag member (A).

Preferably, of the bag members (A) and (B), a slit is arranged only in the bag member (A) so as to pierce the bag member (A) in a thickness direction thereof.

Preferably, a slit is arranged in the heat-sealed portion so as to pierce the bag member (A) and the bag member (B) in a thickness direction thereof.

Preferably, a slit is arranged in the heater-free portion so as to pierce the bag member (A) and the bag member (B) in a thickness direction thereof.

Preferably, the stretchable film of the bag member (B) is comprised of a thermoplastic elastomer.

More preferably, the nonwoven fabric layers of the bag member (A) and bag member (B) each are independently comprised of a spunlace nonwoven fabric.

Further, in the present invention, a bag member for a disposable warmer comprises at least a layered structure with a porous film and a nonwoven fabric layer composed of an elastic nonwoven fabric, and a slit is arranged only in the porous film.

Disposable warmers according to the present invention have the above structures, thereby show good stretchability while maintaining sufficient strength. These disposable warmers enable easy, convenient, and comfortable wearing and are industrially useful.

BRIEF DESCRIPTION OF THE SYMBOLS (A) Bag member (A)
1a Nonwoven fabric layer
1b Porous film
(B) Bag member (B)
2a Nonwoven fabric layer
2b stretchable film
3 Heater
4 Pressure-sensitive adhesive layer (for attachment of a warmer to an adherend)
5, 51, 52, 53 Slit
5a, 5a-1 Linear slit
5b, 5b', 5b-2, 5b-3, 5b-4 Perforated slit
6 Heat-sealed portion
7 Portion with heater sealed therein
8 Heater-free portion
9, 10 Bag member of prior art
105b Slit of prior art

DESCRIPTION OF THE PREFERRED EMBODIMENTS

Figure 5:
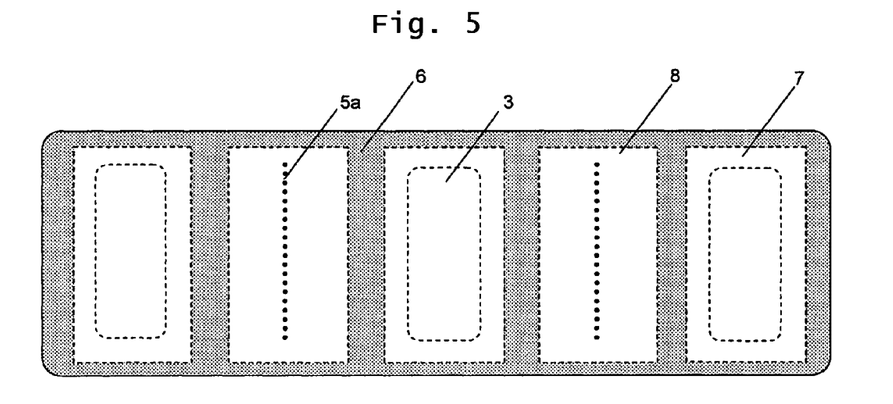
FIG. 5 is a schematic top view, seen from above (opposite side to be attached to an adherend), of the disposable warmer of FIG. 1 with linear slits.
Figure 6:
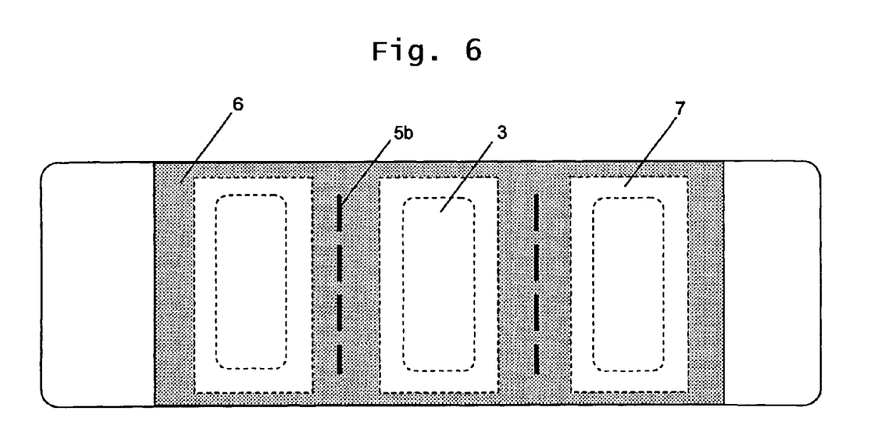
FIG. 6 is a schematic top view, seen from above (opposite side to be attached to an adherend), of the disposable warmer of FIG. 4 with perforated slits.

Disposable warmers according to the present invention will be illustrated in detail with reference to the attached drawings where necessary. FIGS. 1 to 4 are schematic cross-portional views of disposable warmers according to embodiments of the present invention. FIGS. 5 and 6 are schematic top views, seen from above (opposite side to be attached to an adherend), of the disposable warmers of FIGS. 1 and 4, respectively. The disposable warmers according to embodiments of the present invention each include a bag member (A) composed of a layered material of a porous film 1b and a nonwoven fabric layer 1a; and a bag member (B) composed of a layered material of a stretchable film 2b and a nonwoven fabric layer 2a, in which the bag member (A) and the bag member (B) are heat-sealed in a heat-sealed portion 6 to form a bag. For example, the pressure-sensitive adhesive layer 4 is provided in the side to be attached to an adherend, however, the layer 4 may not be provided.

The disposable warmers each include at least two types of portions, i.e., a portion 6 where the bag member (A) and the bag member (B) are heat-sealed (hereinafter referred to as "heat-sealed portion"), and a portion 7 surrounded by the heat-sealed portion 6 and having a heater sealed therein (hereinafter referred to as "portion with a heater sealed therein"). The disposable warmers each include two or more portions 7 with heaters sealed therein. For further improving their stretchability, they preferably further include a portion 8, that is not heat-sealed and has no heater (hereinafter referred to as "heater-free portion"), in addition to the heat-sealed portions 6 and the portions 7 with heaters sealed therein. When the heater-free portion 8 is provided, the portions 7 with heaters sealed therein and the heater-free portion 8 can be arranged in any manner, as long as the heater-free portion 8 resides at least in one region between the two portions 7, with heaters sealed therein, adjacent to each other. In a preferred embodiment, the portions 7 with heaters sealed therein and the heater-free portions 8 are arranged in alternate order as illustrated in FIG. 1.

In the disposable warmers, at least the porous film in the bag member (A) should have a slit or slits in at least one region between a portion with a heater sealed therein and another adjacent portion with a heater sealed therein (hereinafter referred to as "between the portions with heaters sealed therein"). The disposable warmers have dramatically improved stretchability, by slitting at least the porous film, which has poorest stretchability among nonwoven fabrics and films constituting the bag members (A) and (B). In addition, the disposable warmers have further improved stretchability, by slitting in at least one region between the portions with heaters sealed therein to impart stretchability to the entire disposable warmers.

Figure 1:
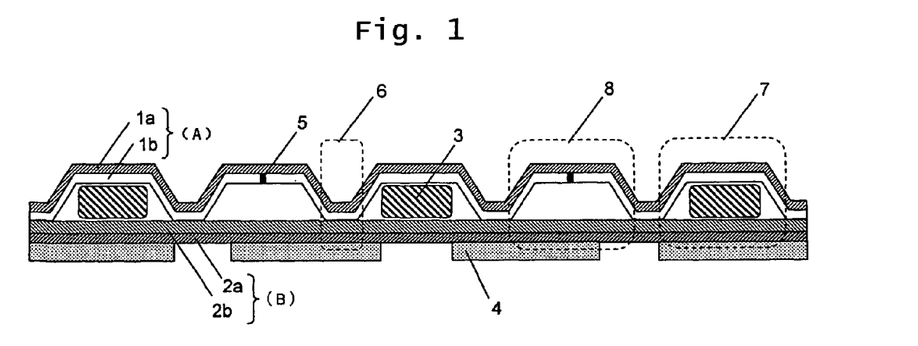
FIG. 1 is a schematic cross-portional view of a disposable warmer according to an embodiment of the present invention, in which only the porous film of the bag member (A) has a slit.
Figure 2:
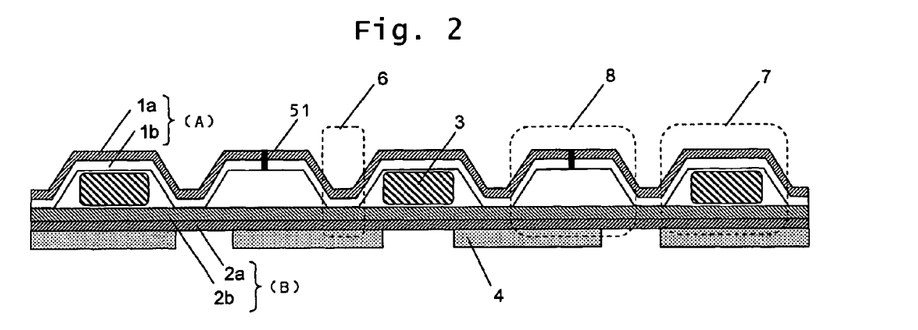
FIG. 2 is a schematic cross-portional view of a disposable warmer according to another embodiment of the present invention, in which only the bag member (A) has a slit that pierces the bag member (A) in its thickness direction.
Figure 3:
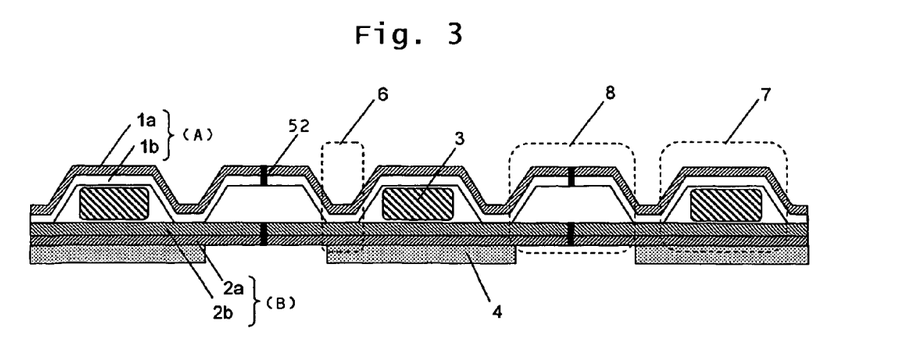
FIG. 3 is a schematic cross-portional view of a disposable warmer according to another embodiment of the present invention, in which the bag member (A) and the bag member (B) in heater-free portions have a slit that pierces the members (A) and (B) in their thickness direction.
Figure 4:
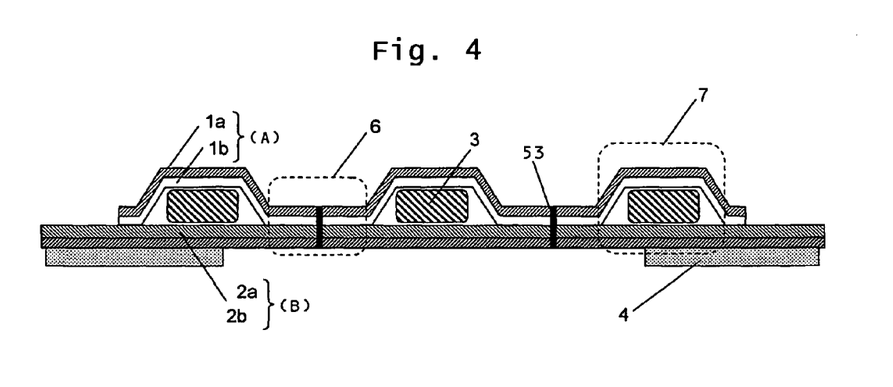
FIG. 4 is a schematic cross-portional view of a disposable warmer according to another embodiment of the present invention, in which the bag member (A) and the bag member (B) in heat-sealed portions have a slit that pierces the members (A) and (B) in their thickness direction.

The way how the slit or slits are arranged is, for example, such that step (i) the slit or slits are arranged only in the porous film of the bag member (A) of the bag members (A) and (B), as illustrated typically in FIG. 1, reference number 5; step (ii) the slit or slits are arranged only in the bag member (A) so as to pierce the bag member (A) in its thickness direction, as illustrated typically in FIG. 2, reference number 51; and step (iii) the slit or slits are arranged in the bag members (A) and (B) so as to pierce the bag members (A) and (B) in their thickness direction, as illustrated typically in FIG. 3, reference number 52 and in FIG. 4, reference number 53.

Even when the slit or slits are arranged only in the porous film having poor stretchability of the bag member (A) as in the step (i), the resulting disposable warmer shows sufficiently satisfactory stretchability, because the bag member (B) includes a stretchable film (elastic film) and thereby has relatively satisfactory stretchability. When the slit or slits are arranged as in the step (i), the disposable warmer further excels in strength when it expands and contracts, because it has no slit that pierces the bag members (A) and (B). Additionally, the disposable warmer is also good in appearance and is pleasant to touch (good in texture), because it has no opening of slit in its surface.

On the other hand, a disposable warmer according to the step (ii) is superior in processability to a disposable warmer according to the step (i), although somewhat inferior in appearance and texture to the disposable warmer according to the step (i). Further, a disposable warmer according to the step (ii) is superior in strength to the step (iii). A disposable warmer according to the step (iii) excels in air permeability and, if sweated, the disposable warmer has capability of letting sweat escape, because it has a slit that pierces the bag members (A) and (B), although somewhat inferior in strength to the disposable warmers according to the steps (i) and (ii).

The slit or slits have only to be arranged in at least one region between the portions with heaters sealed therein, and how and where they are arranged is not particularly limited. However, when the slit or slits are arranged only in the bag member (A) as in the step (i) or (ii), the slit or slits are preferably arranged in a heater-free portion arranged between the portions with heaters sealed therein. By arranging the slit or slits in the heater-free portion, the slit or slits most effectively act to allow the porous film to deform. In the step (iii), the slit or slits may be arranged in the heat-sealed portion as illustrated typically in FIG. 4, reference number 53 and/or may be arranged in the heater-free portion as illustrated typically in FIG. 3, reference number 52.

A disposable warmer according to the present invention may further have a slit or slits in a region other than between the portions with heaters sealed therein. Typically, it may have a slit or slits at an end in a region other than between the portions with heaters sealed therein (e.g., between an end of the disposable warmer and the portion with a heater sealed therein). It should be noted, however, no slit is arranged in the portions with heaters sealed therein.

The bag member (A) for use in the disposable warmers is a layered material structurally including at least a porous film 1b and a nonwoven fabric layer 1a. The bag member (A) has this structure and thereby has capabilities typically of permeating air and supplying oxygen to a heater.

The porous film 1b for use in the bag member (A) is not particularly limited, but can be any porous base film in the form of a film composed of, for example, an olefinic resin. The porous film 1b may have a single-layer structure or a multi-layer structure that is composed of one member or two or more different members.

Examples of the porous film 1b include films composed of a heat sealable layer and/or a film layer. The porous film 1b preferably has heat sealability, because it will be heat-sealed with the bag member (B). Such heat-sealable porous films include a single-layer porous film that has heat sealability; and a multilayer porous film as a layered material of a heat-sealable layer and a film layer having no heat sealability. The heat sealable layer and the film layer may each have a single-layer or multi-layer structure.

The heat sealable layer and the single-layer porous film that has heat sealability can be each formed from a heat-sealable resin composition containing a heat-sealable resin. Such heat-sealable resins are not particularly limited, but are preferably olefinic resins. The olefinic resins can be any resins that contain at least an olefinic component as a monomer component. Examples of the olefinic component are $\alpha$-olefins such as ethylene, propylene, butene-1, pentene-1, hexene-1,4-methyl-pentene-1, heptene-1, and octene-1. Specific examples of the olefinic resins include ethylenic resins such as low-density polyethylenes, linear low-density polyethylenes (straight-chain low-density polyethylenes), medium-density polyethylenes, high-density polyethylenes, ethylene-vinyl acetate copolymers, and ethylene-$\alpha$-olefin copolymers (e.g., ethylene-propylene copolymers); propylene resins such as polypropylenes and propylene-$\alpha$-olefin copolymers; polybutene resins such as polybutene-1; and other olefinic resins such as poly-4-methylpentene-1. Examples of the olefinic resins further include ethylene-unsaturated carboxylic acid copolymers such as ethylene-acrylic acid copolymers and ethylene-methacrylic acid copolymers; ionomers; ethylene-(meth)acrylic ester copolymers such as ethylene-methyl acrylate copolymers, ethylene-ethyl acrylate copolymers, and ethylene-methyl methacrylate copolymers; and ethylene-vinyl alcohol copolymers. Ethylenic resins are preferred as olefinic resins, of which low-density polyethylenes, linear low-density polyethylenes, and ethylene-$\alpha$-olefin copolymers are more preferred.

The $\alpha$-olefin component in the ethylene-$\alpha$-olefin copolymers can be any $\alpha$-olefin other than ethylene, and examples thereof include $\alpha$-olefins having three to ten carbon atoms, such as propylene, butene-1, pentene-1, hexene-1,4-methyl-pentene-1, heptene-1, and octene-1. Specific examples of the ethylene-$\alpha$-olefin copolymers include ethylene-propylene copolymers and ethylene-(butene-1) copolymers. The $\alpha$-olefin component in the propylene-$\alpha$-olefin copolymers as the olefinic resins can be selected as appropriate from among $\alpha$-olefins having, for example, four to ten carbon atoms.

Each of these heat-sealable resins can be used alone or in combination.

Among heat-sealable resin compositions containing these resins, olefinic resin compositions containing at least an ethylene-$\alpha$-olefin copolymer as the olefinic resin are preferred, of which olefinic resin compositions containing an ethylene-$\alpha$-olefin copolymer, and a low-density polyethylene and/or a linear low-density polyethylene are more preferred. In such olefinic resin compositions containing at least an ethylene-$\alpha$-olefin copolymer, or in the olefinic resin compositions containing an ethylene-$\alpha$-olefin copolymer and a low-density polyethylene and/or linear low-density polyethylene, the content of the ethylene-$\alpha$-olefin copolymers is not particularly limited and may be, for example, 5 percent by weight or more, preferably 10 to 50 percent by weight, and more preferably 15 to 40 percent by weight, based on the total weight of olefinic resins.

For carrying out heat sealing at lower temperatures and higher speed, it is effective to use heat-sealable resins having lower melting points. Among such resins, low-density polyethylenes prepared by the catalysis of metallocene catalysts are more effective.

Specifically, as the heat-sealable layer and single-layer porous film that has heat sealability, polyolefin porous films are preferred, of which polyethylene porous films are more preferred.

The film layer having no heat sealability to be stacked or laminated with the heat-sealable layer can be any film layer composed of a known or common resin film. Examples of resins for constituting the film layer include polyester resins and olefinic resins. Among them, olefinic resins are preferred for their low cost and excellent flexibility. The olefinic resins can be any known or common olefinic resins.

The porous film may be a non-oriented film or a uniaxially or biaxially oriented film, but is preferably a non-oriented film. When masking property is desired, the porous film may further contain fillers such as white titanium pigment.

The thickness of the porous film is not particularly limited and is, for example, about 10 to 500 μm, preferably 12 to 200 μm, and more preferably 20 to 150 μm. Where necessary, the porous film may have been subjected to a treatment of every kind, such as backing and/or antistatic treatment.

Nonwoven fabrics for use in the nonwoven fabric layer 1a of the bag member (A) are not particularly limited and include known or common nonwoven fabrics including those of natural fibers, and those of synthetic resins, such as nylon nonwoven fabrics (polyamide nonwoven fabrics), polyester nonwoven fabrics, polyolefin nonwoven fabrics, and rayon nonwoven fabrics. The nonwoven fabrics 1a may be prepared according to any process and can be, for example, those prepared by spunbonding (spunbonded nonwoven fabrics) or those prepared by spunlacing (spunlace nonwoven fabrics). Among them, spunlace nonwoven fabrics are preferred for higher stretchability. In addition, for further higher stretchability, elastic nonwoven fabrics are preferred, which use thermoplastic elastomers as resins for constituting fibers of nonwoven fabrics. Examples of thermoplastic elastomers for use in the elastic nonwoven fabrics include thermoplastic elastomers such as styrenic elastomers, polyester elastomers, and urethane elastomers, as exemplified in the after-mentioned stretchable films. The nonwoven fabrics may have a single-layer structure or a multi-layer structure. The fiber diameter, fiber length, mass per unit area, and other parameters of the nonwoven fabric are not particularly limited. However, the nonwoven fabric preferably has a mass per unit area of about 20 to 100 $g/m^2$, and more preferably 20 to 80 $g/m^2$, for satisfactory processability and cost efficiency. The nonwoven fabric may be composed of a fiber of one type or fibers of different types.

In the bag member (A), the way how the porous film 1b and the nonwoven fabric layer 1a are stacked or laminated is not particularly limited, but they are preferably bonded through an adhesive. The adhesive is not particularly limited, and examples thereof include rubber adhesives such as natural rubber and styrenic elastomers; urethane adhesives such as acrylic urethanes; acrylic adhesives; silicone adhesives; polyester adhesives; polyamide adhesives; epoxy adhesives; vinyl alkyl ether adhesives; fluorine-containing adhesives; and other known adhesives. Each of these adhesives can be used alone or in combination. Among them, amide adhesives and polyester adhesives are preferred.

Adhesives for use herein can be adhesives of every form, and are not particularly limited, of which hot-melt (thermofusible) adhesives are particularly preferred, because they can be applied by heating and melting without solvents, can be directly applied even to nonwoven fabrics to form an adhesive layer, and can give further higher adhesive strength in the heat-sealed portion as a result of heat sealing. Specifically, the adhesives are preferably amide or polyester hot-melt adhesives, of which thermoplastic amide or polyester hot-melt adhesives are more preferred.

The specific way how the porous film 1b and the nonwoven fabric layer 1a are laminated varies depending typically on the type of adhesive and is not particularly limited. When a hot-melt adhesive is used, for example, the lamination is preferably carried out by applying the adhesive to a nonwoven fabric layer, and bonding a base film thereonto. The application can be carried out using any known or common procedure used for the application of hot-melt adhesives and is not particularly limited. Typically, when a porous film is used as the base film, the application is preferably carried out by spray coating, stripe coating, or dot coating, for maintaining the air permeability. On the other hand, when an airtight base film is used, spray coating, stripe coating or full coating (full width coating) may be employed. The residual amount to be solidified of applied adhesive is not particularly limited, but is preferably 0.5 to 20 $g/m^2$, and more preferably 1 to 8 $g/m^2$, from the viewpoints of adhesion of the heat-sealed portion and economical efficiency upon the formation of bag of the warmer.

In the bag member (A), the porous film 1b and the nonwoven fabric layer 1a may be entirely completely bonded (sealed) or bonded only in the heat-sealed portion 6. It is also acceptable that the heat-sealed portion 6 is firmly bonded, and the other portions than the heat-sealed portion 6 are temporarily adhered and stacked (hereinafter simply referred to as "temporary adhesion"). In a preferred embodiment, the porous film 1b and the nonwoven fabric layer 1a are laminated in temporary adhesion in the other portions than the heat-sealed portion 6, for further higher stretchability. As used herein "temporary adhesion" refers to a condition where these layers sufficiently adhere to each other upon manufacturing and processing of bag members and disposable warmers, but they are capable of detaching from each other by the action of external force applied upon the use of disposable warmers. More specifically, "temporary adhesion" refers to that the peel force between the porous film 1b and the nonwoven fabric layer 1a before heat sealing is 0.2 N/25-mm or less, as determined in a T-peel test at a rate of pulling of 300 mm/minute. The peel force is preferably 0.1 N/25-mm or less, and more preferably 0.0001 to 0.1 N/25-mm. When the porous film 1b and the nonwoven fabric layer 1a are attached with a peel force within the above-specified range (i.e., when they are in temporary adhesion," the film and layer show good productivity and processability because they are bonded at a sufficient adhesive strength upon manufacturing and processing. On the other hand, the warmers show further higher stretchability, because the porous film 1b and the nonwoven fabric layer 1a will detach from each other when the warmers are expanded and contracted. When the peel force between the film and layer is more than 0.2 N/25-mm, a disposable warmer may have poor stretchability, because the porous film and the nonwoven fabric layer are difficult to detach from each other when the warmers are expanded and contracted.

In the heat-sealed portion 6, the porous film 1b and the nonwoven fabric layer 1a are preferably firmly bonded. The adhesive strength (peel force) between the porous film 1b and the nonwoven fabric layer 1a in the heat-sealed portion 6 is preferably 3.0 N/25-mm or more, and more preferably 5.0 to 20.0 N/25-mm. A disposable warmer having the adhesive strength in the heat-sealed portion 6 of less than 3.0 N/25-mm may suffer from delamination between the porous film 1b and the nonwoven fabric layer 1a in the heat-sealed portion 6 when used as a disposable warmer.

In order to control the porous film 1b and the nonwoven fabric layer 1a to be in temporary adhesion, for example, the surface tension of a side of the porous film 1b to face the nonwoven fabric layer 1a is preferably adjusted to 30 to 45 dyne/cm, and more preferably 33 to 40 dyne/cm. For controlling the surface tension to this range, it is preferred, for example, no corona processing is applied to the surface of the porous film 1b.

For controlling the porous film 1b and the nonwoven fabric layer 1a to be in temporary adhesion, the porous film 1b and the nonwoven fabric layer 1a are attached at temperatures of preferably 40° C. to 110° C., more preferably 60° C. to 100° C., and further preferably 60° C. to 95° C. The attaching temperature significantly affects the adhesive strength (peel force). If it is lower than 40° C., the adhesive strength may be excessively low, whereby the productivity may insufficient. If it is higher than 110° C., the adhesive strength may be excessively high to fail to achieve temporary adhesion.

The bag member (B) for use in the disposable warmers is a layered material structurally including at least a stretchable film 2b and a nonwoven fabric layer 2a. The bag member (B) structurally has the stretchable film 2b, thereby shows good stretchability, and acts to impart flexibility and stretchability to the disposable warmers. If a non-stretchable base film, such as a non-stretchable polyolefin film, is used instead of a stretchable film 2b in a bag member (B), it is difficult to impart sufficient stretchability even when a slit or slits are provided. On the contrary, if large slits are arranged to deform or stretch sufficiently, the disposable warmer has insufficient strength. Specifically, it is difficult to provide both sufficient strength and satisfactory stretchability of the disposable warmer in this case.

The stretchable film 2b for use in the bag member (B) has, for example, a 20%-tensile modulus of elasticity of 6.4 (N/mm$^2$) or less and a permanent strain after 20%-tension of 10% or less. Preferably, the 20%-tensile modulus of elasticity is 4.8 (N/mm$^2$) or less, and more preferably 3.2 (N/mm$^2$) or less. Preferably, the permanent strain after 20%-tension is 8% or less, and more preferably 6% or less.

The 20%-tensile modulus of elasticity and permanent strain may be determined in the following manner using a tensile tester. Initially, a sample piece having a width in machine direction of 25 mm and a length in transverse direction of 100 mm is sampled from a film (stretchable film) to give a strip sample piece having a length of 100 mm and a width of 25 mm. Gauge lines at 50 mm intervals are marked at a center part in a longitudinal direction of the sample piece; the sample piece is held between a chuck so that the chuck interval (measurement length) stands at 50 mm; and a measurement is carried out. The stress at the time when the sample piece is pulled 10 mm (20% elongation) at a rate of pulling of 300 mm/minute is defined as the "20%-tensile modulus of elasticity."

Figure 15:
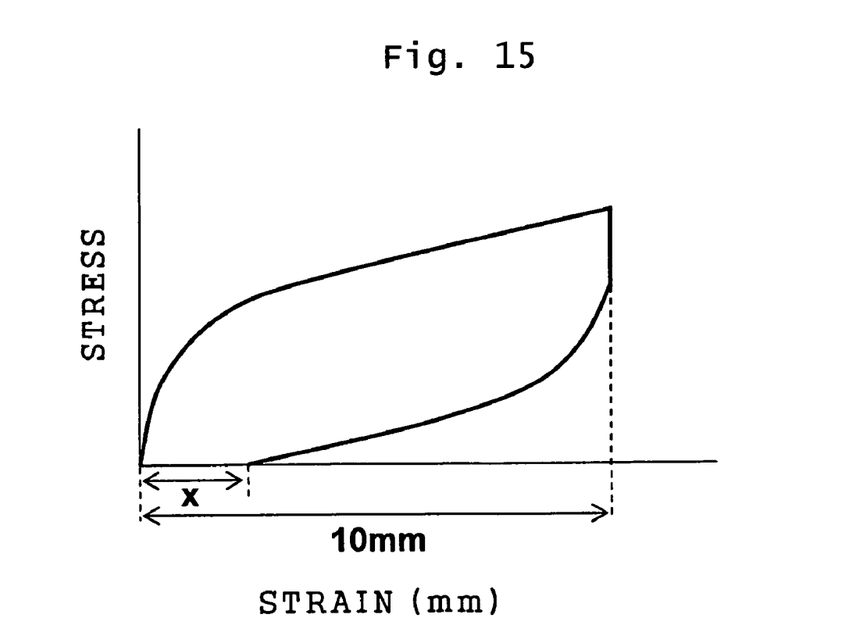
FIG. 15 schematically illustrates a stress-strain curve in a tensile test for measuring "20%-tensile modulus of elasticity" and "permanent strain" of stretchable films.

Next, the pulling is stopped at the point of 10 mm-tension (20% elongation), the sample piece is left under this condition for 1 minute and is returned at a rate of 300 mm/minute to the initial chuck interval (50 mm). In a stress-strain curve obtained herein, the distance "x" (strain at the point where the stress becomes zero) between the point where the stress becomes zero to the zero point (the point of origin of stress-strain curve) is measured in unit of millimeter, the measured distance "x" is divided by the initial chuck interval 50 mm, and the divided value is multiplied by 100. Thus, the permanent strain in unit of percentage is determined by calculation according to the following equation (see FIG. 15):

Permanent strain(%)=(x/50)×100

In other words, the "permanent strain" refers to the strain (%) at the point where the stress becomes zero in a stress-strain curve when the sample piece is left in 20% elongation for 1 minute and, then, the chuck interval is returned to initial one.

Resins for constituting the stretchable film 2b are preferably thermoplastic elastomers such as styrenic elastomers, olefinic elastomer, polyester elastomers, and urethane elastomers. Among them, styrenic elastomers and olefinic elastomers are particularly preferred for their good heat sealability with polyolefin porous films.

The styrenic elastomers include copolymers composed of a styrene monomer unit and the other copolymerizable components, such as ethylene, propylene, butylene, and alkyl (meth) acrylates, of which block copolymers are preferred; and hydrogenated derivatives of these. Preferred examples of styrenic elastomers include styrene-butadiene copolymers (SB), styrene-isoprene copolymers (SI), styrene-isoprene-styrene block copolymers (SIS), styrene-butadiene-styrene block copolymers (SBS), styrene-ethylene-butylene-styrene block copolymers (SEBS), styrene-ethylene-propylene-styrene block copolymers (SEPS), styrene-ethylene-isoprene-styrene block copolymers (SIPS), and styrene-ethylene-propylene block copolymers (SEP). Among them, SEBS and SEPS are more preferred, for their further satisfactory heat sealability.

Preferred examples of the olefinic elastomers include "Toughmer" (α-olefinic copolymer) supplied by Mitsui Chemicals, Inc., ethylene-vinyl acetate copolymers (EVA), and ethylene-methacrylic acid copolymers (EMA).

Each of these thermoplastic elastomers can be used alone or in combination. Known or common olefinic resins such as polyethylenes can also be used in combination with these thermoplastic elastomers.

Nonwoven fabrics for constituting the nonwoven fabric layer 2a in the bag member (B) are not particularly limited, as long as they do not adversely affect the stretchability of the stretchable film in a direction where the disposable warmer should expand and contract (for example, transverse or longitudinal direction of the warmer). They can be suitably selected typically from among the nonwoven fabrics listed as the nonwoven fabric constituting the nonwoven fabric layer 1a in the bag member (A). Among them, spunlace nonwoven fabrics are particularly preferred, because they can expand with a weak stress.

The way how the stretchable film 2b and the nonwoven fabric layer 2a are stacked in the bag member (B) may be as with the lamination procedure in the bag member (A). How the stretchable film 2b and the nonwoven fabric layer 2a are laminated in the bag member (B) is not particularly limited, but the film and layer are preferably laminated in temporary adhesion, as in the bag member (A).

Any of the bag members (A) and (B) can be used as a member facing an adherend when the disposable warmer is attached to the adherend (the member hereinafter also referred to as "backing member"), and as another member arranging opposite side to an adherend (the member hereinafter also referred to as "top member"). It is not particularly limited that which member (A) or (B) is used for the backing or top member. For ensuring higher air permeability of the porous film, it is desirable to use the bag member (A) as the top member, and the bag member (B) as the backing member.

Of the bag members (A) and (B), one used as the backing member may further include, where necessary, a pressure-sensitive adhesive layer 4 to allow the warmer to be attached to the adherend. The pressure-sensitive adhesive layer 4 is arranged on the nonwoven fabric layer. The pressure-sensitive adhesive is not particularly limited, and includes, for example, rubber pressure-sensitive adhesives, urethane pressure-sensitive adhesives (acrylic urethane pressure-sensitive adhesives), acrylic pressure-sensitive adhesives, silicone pressure-sensitive adhesives, polyester pressure-sensitive adhesives, polyamide pressure-sensitive adhesives, epoxy pressure-sensitive adhesives, vinyl alkyl ether pressure-sensitive adhesives, fluorine pressure-sensitive adhesives, and other known pressure-sensitive adhesives. Each of the pressure-sensitive adhesives can be used alone or in combination. Among them, rubber and urethane (acrylic urethane) pressure-sensitive adhesives are particularly preferred.

Examples of the rubber pressure-sensitive adhesives include rubber pressure-sensitive adhesives containing natural rubbers and synthetic rubbers of every kind as base polymers. Examples of rubber pressure-sensitive adhesives containing synthetic rubbers as base polymers include styrenic rubbers (also referred to as "styrenic elastomers") such as styrene-butadiene (SB) rubbers, styrene-isoprene (SI) rubbers, styrene-isoprene-styrene block copolymer (SIS) rubbers, styrene-butadiene-styrene block copolymer (SBS) rubbers, styrene-ethylene-butylene-styrene block copolymer (SEBS) rubbers, styrene-ethylene-propylene-styrene block copolymer (SEPS) rubbers, styrene-ethylene-isoprene-styrene block copolymer (SIPS) rubbers, and styrene-ethylene-propylene block copolymer (SEP) rubbers; polyisoprene rubbers; reclaimed rubbers; butyl rubbers; polyisobutylenes; and modified derivatives of these. Among them, pressure-sensitive adhesives of styrenic elastomers are preferred, of which SIS and SBS are more preferred. Each of these can be used alone or in combination.

The urethane pressure-sensitive adhesives can be any known or common urethane pressure-sensitive adhesives, and are not particularly limited. Preferred examples thereof include urethane pressure-sensitive adhesives listed in Japanese Patent No. 3860880 and JP-A No. 2006-288690. Among them, acrylic urethane pressure-sensitive adhesives composed of isocyanate/polyester polyol are more preferred. For mitigating a skin irritation when the warmer is directly attached to the skin, the acrylic urethane pressure-sensitive adhesives are preferably foamed pressure-sensitive adhesives containing foam (bubbles). Such foamed pressure-sensitive adhesives can be prepared, for example, adding known or common blowing agents to pressure-sensitive adhesives.

These pressure-sensitive adhesives may be pressure-sensitive adhesives of any form, such as emulsion pressure-sensitive adhesives, solvent-containing pressure-sensitive adhesives, and hot-melt pressure-sensitive adhesives. Among them, hot-melt pressure-sensitive adhesives (thermofusible pressure-sensitive adhesives) are preferably used, because they can be applied by heating and melting without using solvents and can be directly applied even to a porous surface (e.g., a surface of a nonwoven fabric) to form a pressure-sensitive adhesive layer.

The application of the pressure-sensitive adhesive to the bag member can be carried out by any known or common coating procedure, such as roll coating, die coating, gravure coating, bar coating, melt blowing, or curtain spraying. The pressure-sensitive adhesive layer may be formed, for example, in stripes by stripe coating or in dots partially by dot coating.

Suitable coating amount (solids content, the residual amount to be solidified) can be set according typically to the type of pressure-sensitive adhesive and is, for example, about 10 to 200 g/m$^2$, and preferably 15 to 150 g/m$^2$.

The pressure-sensitive adhesive-coated layer may be subjected to a treatment such as drying, thermal curing, and/or curing by an active energy ray, whereas the treatment may vary depending typically on the type of pressure-sensitive adhesive and is not particularly limited. A heating procedure for use typically in the drying or thermal curing of the coated layer is not particularly limited and includes, for example, any known heating procedures such as heating with an electric heater and heating with electromagnetic waves such as infrared rays. When the coated layer is cured by the application of an active energy ray in the curing by an active energy ray, the application procedure is not particularly limited and can be suitably selected from among known procedures including ultraviolet ray application using known ultraviolet lamps such as electrode-type high-pressure mercury lamps, ozoneless lamps, metal halide lamps, and electrode-less microwave lamps.

The thickness (thickness after drying and/or curing) of pressure-sensitive adhesive layer is preferably about 10 to 200 μm, and more preferably about 15 to 150 μm, from the viewpoints of adhesive strength and cost.

A disposable warmer according to the present invention can be prepared by heat sealing the bag members (A) and (B) so that the surface of porous film 1b faces the surface of stretchable film 2b, to form a bag, and placing a heater 3 in the bag. The heat sealing may be carried out using any procedure and device, and is not particularly limited, but is preferably carried out by bonding with press using a heat sealer. For firm bonding, the heat sealing temperature in the bonding with press using a heat sealer is preferably 90° C. to 250° C., and more preferably 130° C. to 200° C.; and the pressure is preferably 0.5 to 30 kg/cm$^2$, and more preferably 2.0 to 10 kg/cm$^2$. The heat sealing period is preferably 0.02 to 1.0 second, and more preferably 0.05 to 0.5 second, for satisfactory productivity. The width of heat sealing (heat sealing width) is not particularly limited, but is preferably 1.0 to 20.0 mm, and more preferably 2.0 to 10.0 mm.

Disposable warmers according to the present invention include portions 7 with heaters sealed therein where a heater 3 is sealed in a bag. Where necessary, they further include one or more heater-free portions 8 having no heater.

Portion with a Heater Sealed Therein

The portions 7 with heaters sealed therein are portions that include a heater 3 sealed in a bag which has been prepared by heat sealing of the bag members (A) and (B). The disposable warmers each have two or more portions 7 with heaters sealed therein. Preferably, they have three to twenty portions 7 with heaters sealed therein, and more preferably three to ten portions 7 with heaters sealed therein. Each of the portions 7 with heaters sealed therein is surrounded by a heat-sealed portion 6 in plane of the warmer and is thereby independent from other portion 7 with a heater sealed therein(s) and heater-free portion(s) 8. Arranging two or more divided or independent portions 7 with heaters sealed therein, the warmer becomes bendy and has improved flexibility and improved wearing comfort. If a disposable warmer has only one portion 7 with a heater sealed therein, the disposable warmer may not be bendy and may have poor flexibility and inferior wearing comfort, because iron particles generally used as a heater for such disposable warmers may aggregate with each other upon oxidation to make solid as a whole, and the solidified heater acts like a "plate". On the other hand, if a disposable warmer has portions 7 with heaters sealed therein in a number exceeding twenty, the warmer may have poor productivity, and, in addition, may exhibit insufficient warming function, because the amount of the heater decreases and becomes relatively insufficient.

The heater to be sealed in the portion 7 with a heater sealed therein can be a heater for use in known disposable warmers, is not particularly limited, and examples thereof include metal powders such as iron powder; activated carbon; water; water retention agents such as wood powder, vermiculite, diatomaceous earth, pearlite, silica gel, alumina, and water-absorptive resins; and sodium chloride.

Heater-Free Portion

Figure 8:
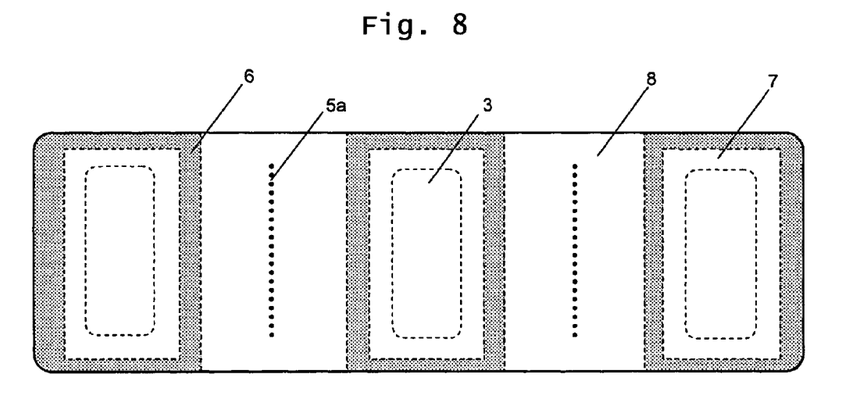
FIG. 8 is a schematic top view, seen from above (opposite side to be attached to an adherend), of a disposable warmer having cylindrical heater-free portions, according to an embodiment of the present invention.

The heater-free portion 8 is a portion that has not been heat-sealed and has no heater. The portion 8 is not necessarily surrounded by a heat-sealed portion 6. Typically, the portion 8 may be a bag-like portion surrounded by a heat-sealed portion 6, as with the portion 7 with a heater sealed therein, (FIG. 5) or a tubular portion, such as a cylindrical portion, which is not fully surrounded by a heat-sealed portion 6 (FIG. 8).

Figure 9:
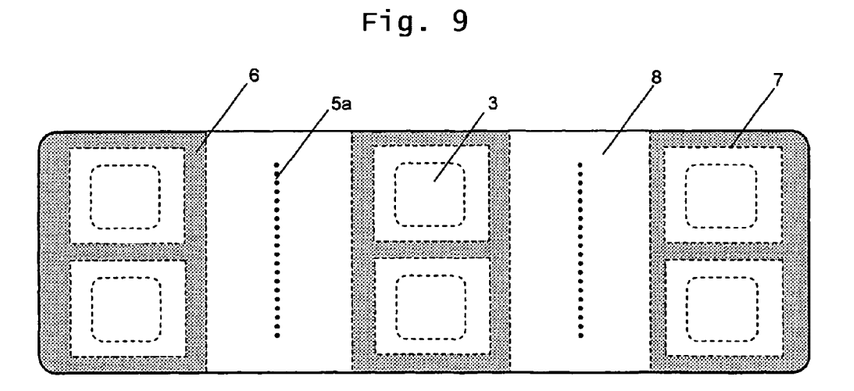
FIG. 9 is a schematic top view, seen from above (opposite side to be attached to an adherend), of a disposable warmer having cylindrical heater-free portions, according to another embodiment of the present invention.

In the present invention, a disposable warmer preferably has a heater-free portion 8 in at least one region between a portion 7 with a heater sealed therein and adjacent another portion 7 with a heater sealed therein (between the portions 7 with heaters sealed therein). More preferably, portions 7 with heaters sealed therein and heater-free portions 8 are arranged in alternate order. The arrangement of these portions may also be one illustrated in FIG. 9.

Slits

As is described above, disposable warmers according to the present invention have a slit (cut) or slits in a heat-sealed portion 6 or a heater-free portion 8 in at least one region between the portions 7 with heaters sealed therein. The slit or slits are preferably arranged in each region between the portions 7 with heaters sealed therein. For maintaining the strength, the slit or slits are preferably arranged, of the bag members (A) and (B), only in the bag member (A), and is more preferably arranged only in the porous film 1b of the bag member (A). Slitting the porous film 1b alone improves the stretchability of disposable warmer while maintaining the strength thereof. When the slit or slits are arranged not only in the porous film 1b but so as to pierce the warmer in a thickness direction, the warmer may have somewhat insufficient strength.

Figure 7:
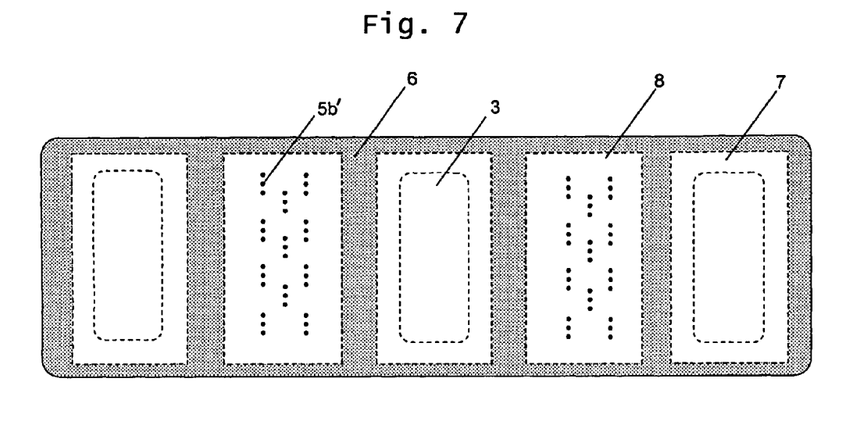
FIG. 7 is a schematic top view, seen from above (opposite side to be attached to an adherend), of a disposable warmer according to another embodiment of the present invention with perforated slits.

The slit has only to be so arranged that regions between portions 7 with heaters sealed therein can expand and contract. Typically, the slit or slits may be arranged in straight lines (FIG. 5; 5a) or may be arranged in perforations (FIG. 6; 5b and FIG. 7; 5b') in a direction perpendicular to the direction where the stretchability of the disposable warmer is mainly required. The slit or slits may also be arranged such that two or more slits in the tapered form tapering down toward the top are arrayed in a vertical direction (widthwise direction). The length of slit(s) is, in the case typically of linear slit(s), preferably 30% to 100%, and more preferably 70% to 100% of the total width of the warmer.

When the slit or slits are arranged only in the bag member (A) or only in the porous film 1b of the bag member (A), they are preferably arranged in a heater-free portion 8 arranged between the portions 7 with heaters sealed therein. Slits, if arranged in the heater-free portion 8, allow the bag member (A) to deform relatively largely, whereas the stretchable film allows the bag member (B) to deform largely. Thus, the entire disposable warmer has further higher stretchability.

The disposable warmers herein employ a stretch film 2b in one bag member (B) to have stretchability. On the other hand, they employ a porous film 1b in the other bag member (A) to have air permeability and oxygen supply ability. However, if a disposable warmer includes a bag formed simply by heat sealing the bag members (A) and (B), the disposable warmer shows insufficient stretchability, because the bag member (A) using a porous film 1b, a non-stretch material, will show insufficient stretchability. In contrast, according to the present invention, a slit or slits are arranged in the porous film 1b of the bag member (A), and this makes the entire disposable warmer sufficiently satisfactorily stretchable, because the slit region expands as the warmer expands, to allow the bag member (A) to deform relatively largely, whereas the bag member (B) exhibits its high stretchability without deterioration of the stretchability.

It may be possible to prepare a highly stretchable disposable warmer by using stretchable films in the two bag members. This technique, however, fails to provide a disposable warmer that has both satisfactory air permeability and/or oxygen supply ability and sufficient stretchability, because such stretchable films are stretchable and flexible to make pores, even if formed, clogged, and this makes it impossible to provide a porous film having satisfactory air permeability and oxygen supply ability by using stretchable films.

A disposable warmer according to the present invention is preferably used as a portable warmer. In another embodiment, a disposable warmer preferably has a pressure-sensitive adhesive layer, and this is preferably used as a disposable warmer to be attached to the body, cloth, or footwear. Because the disposable warmer has the above mentioned structure and is highly stretchable, the warmer is resistant to delamination even when it is attached to a portion that will bend or expand. Therefore, the warmer is good in wearing convenience and is comfortable upon wearing.

The disposable warmer having a pressure-sensitive adhesive layer may further have any known or common release film (separator) in order to protect the pressure-sensitive adhesive layer before use. The disposable warmer is highly stretchable, whereby the release film is easy to peel off upon use, to give excellent convenience upon use.

A disposable warmer according to the present invention is enveloped in an outer pouch and is sold as a warmer product. Base materials constituting the outer pouch are not particularly limited and include plastic base materials; fibrous base materials such as nonwoven fabric base materials and woven fabric base materials made of fibers of every kind); and metallic base materials such as metal foil base materials made of metallic components of every kind). Among them, plastic base materials are preferably used as the base materials. Examples of the plastic base materials include polyolefin base materials such as polypropylene base materials and polyethylene base materials; polyester base materials such as poly(ethylene terephthalate) base materials; styrenic base materials including polystyrene base materials, and styrenic copolymer base materials such as acrylonitrile-butadiene-styrene copolymer base materials; amide resin base materials; and acrylic resin base materials. The base material constituting the outer pouch may have a single layer structure or a multi-layer structure. The thickness of the outer pouch is not particularly limited, but is preferably 30 to 300 µm.

In a preferred embodiment, the outer pouch has a layer having gas barrier properties that inhibit permeation of gaseous components such as oxygen gas and water vapor (gas barrier layer). The gas barrier layer is not particularly limited, and examples thereof include oxygen barrier resin layers such as those made of poly(vinylidene chloride) resins, ethylene-vinyl alcohol copolymers, poly(vinyl alcohol)s, and polyamide resins; water vapor barrier resin layers such as those made of polyolefins and poly(vinylidene chloride)s; and oxygen barrier and/or water vapor barrier inorganic compound layers such as made of elementary metals such as aluminum, and metallic compounds including metal oxides such as silicon oxide and aluminum oxide. The gas barrier layer may be a single layer (e.g., it may be the outer pouch base material itself) or a multilayer layered material.

The outer pouch may be a pouch of any form and structure, such as "four-sided sealed pouch," "three-sided sealed pouch," "pillow style pouch," "stand-up pouch" ("standing pouch"), or "gusseted pouch." In a preferred embodiment, the outer pouch is a four-sided sealed pouch. The outer pouch may be prepared using an adhesive, but it is preferably prepared by heat sealing (thermofusing) as typically in a four-sided heat-sealed pouch.

EXAMPLES

The present invention will be illustrated in further detail with reference to several examples below, which is by no means construed to limit the scope of the present invention.

Example 1

Preparation of Bag Member (A)

A polyamide hot glue (hot melt adhesive) was fibrously applied, in an amount of 5 g/m² by spray coating at 180° C., to one side of a polyester spunlace nonwoven fabric (supplied by YUHO Co., Ltd. under the trade name of "S0040," mass per unit area: 40 g/m²). Next, the coated side was attached by bonding with heat and press at 120° C. to a polyethylene porous film (supplied by Nitto Lifetec Corporation under the trade name of "BREATHRON," thickness: 70 μm). In addition, the porous film 1b alone was linearly cut (half-cut) as illustrated as 5a-1 in FIGS. 10A and 10B to give a bag member (A) (top member).

Preparation of Bag Member (B)

A polyamide hot glue (hot melt adhesive) was fibrously applied, in an amount of 5 g/m² by spray coating at 180° C., to one side of a polyester spunlace nonwoven fabric (supplied by YUHO Co., Ltd. under the trade name of "S0040," mass per unit area: 40 g/m²). Next, the coated side was attached, by bonding with heat and press at 80° C., to a stretchable film 50 μm thick which had been formed by extruding a SEBS elastic resin (supplied by Shell in Japan under the trade name of "Kraton G1657") at 190° C. In addition, a pressure-sensitive adhesive layer (SIS pressure-sensitive adhesives, thickness: 100 μm) was formed on the nonwoven fabric layer, to yield a bag member (B) (backing member).

Preparation of Disposable Warmer

Figure 10:
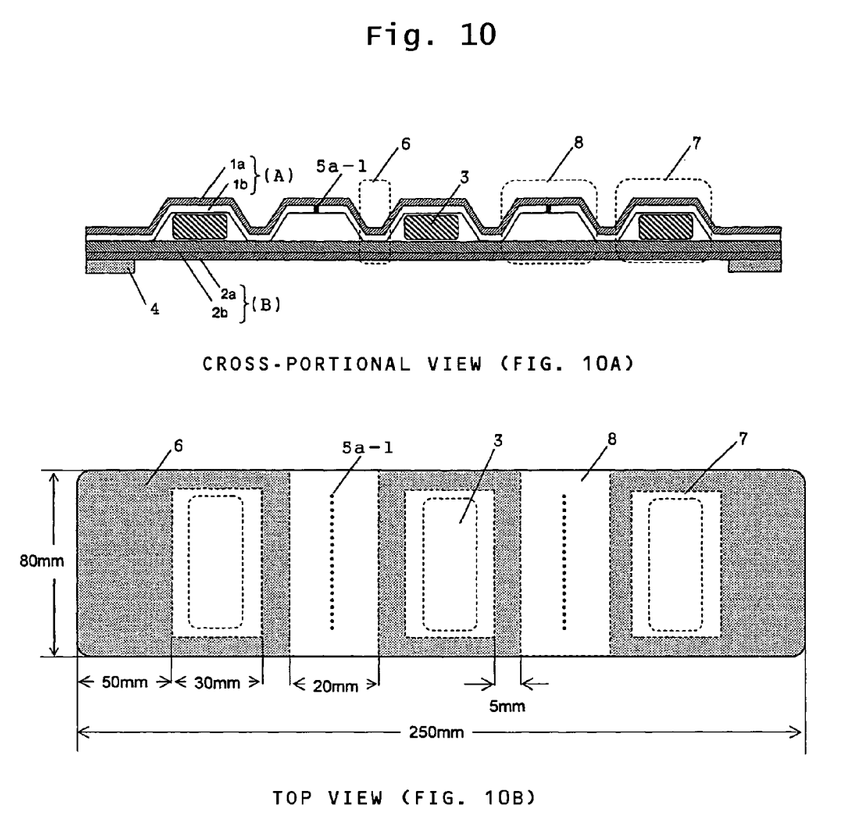
FIGS. 10A and 10B are a schematic cross-portional view and a schematic top view seen from above (opposite side to be attached to an adherend), respectively, of a disposable warmer of Example 1.

The above-prepared bag members (A) and (B) were superposed with each other so that the porous film 1b of the bag member (A) faced the stretchable film 2b of the bag member (B). While placing a heater 3 therein, the bag members (A) and (B) were heat-sealed with the "Fuji Impulse Sealer" supplied by Fujiimpulse Co., Ltd. at 180° C. (scale 4) so that the slits 5a-1 were positioned in heater-free portions 8. Thus, a disposable warmer having the configuration as shown in FIGS. 10A and 10B was prepared. The heater used herein was contents of a commercially available body warmer and was a mixture mainly containing iron powder.

Further, the warmer was placed in an outer pouch, the outer pouch was sealed by heat sealing and thereby yielded a disposable warmer product. The outer pouch used herein was an outer pouch of a commercially available body warmer and was a gas barrier film mainly containing polypropylene.

Example 2

A bag member (A) (top member) was prepared by the procedure of Example 1, except for forming perforated slits 5b-2 that pierce the bag member (A) in its thickness direction. Using this bag member (A), a disposable warmer and a disposable warmer product were prepared by the procedure of Example 1.

Figure 11:
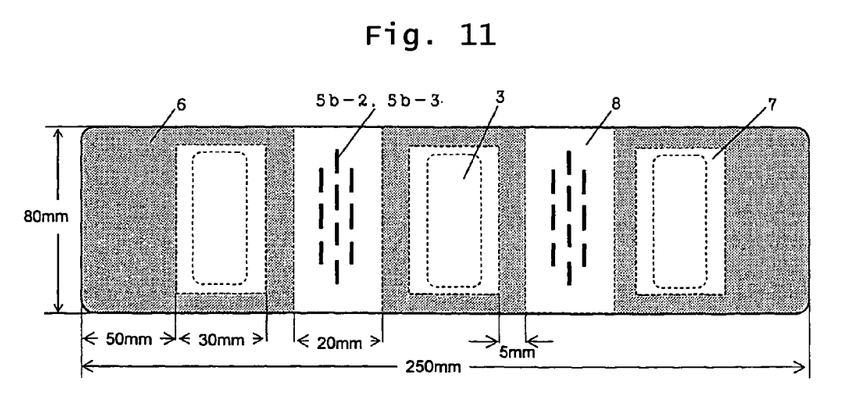
FIG. 11 is a schematic top view, seen from above (opposite side to be attached to an adherend), of disposable warmers of Examples 2 and 3.

How the slits are arrayed in Examples 2 and 3 is illustrated in FIG. 11.

Example 3

Bag members (A) and (B) which had not yet been slit were heat-sealed by the procedure of Example 1. Perforated slits 5b-3 were then formed in heater-free portions 8 so as to pierce the entire body warmer (bag members (A) and (B)). Thus, a disposable warmer and a disposable warmer product were prepared.

Example 4

Figure 12:
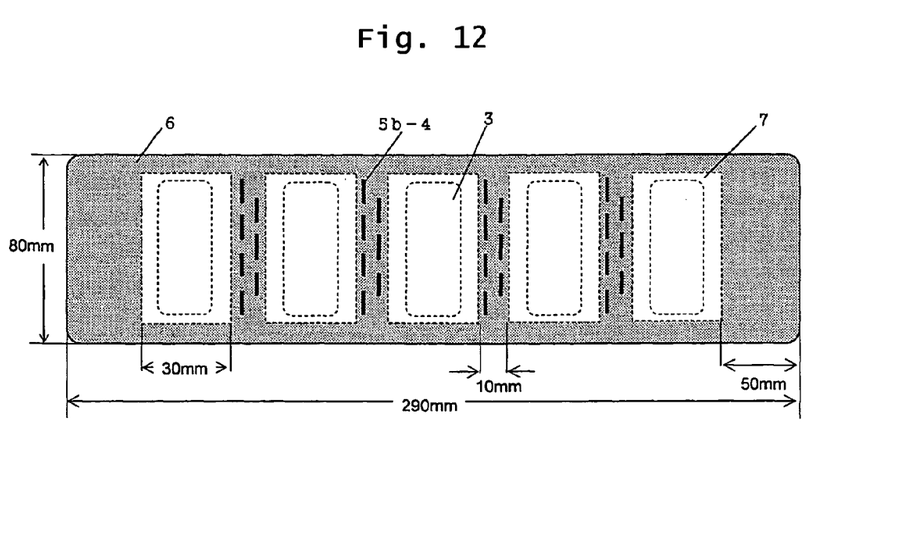
FIG. 12 is a schematic top view, seen from above (opposite side to be attached to an adherend), of a disposable warmer of Example 4.

Bag members (A) and (B) which had not yet been slit were heat-sealed under the same conditions as in Example 1, while sealing a heater 3 therein (FIG. 12). Perforated slits 5b-4 were then formed in heat-sealed portions 6 so as to pierce the entire body warmer (bag members (A) and (B)). Thus, a disposable warmer and a disposable warmer product were prepared.

How the slits are arrayed in the disposable warmer of Example 4 is illustrated in FIG. 12.

Comparative Example 1

A disposable warmer and a disposable warmer product were prepared by the procedure of Example 1, except for forming no slit.

The disposable warmers prepared according to Examples 1 to 4 and Comparative Example 1 were evaluated by the following methods. The results are shown in Table 1.

(1) Stretchability of Disposable Warmer

Both ends of a sample body warmer were pulled by hands in a transverse direction with force of about 10 to 15 N, and the length of the warmer after deformation was measured. The initial lengths of the warmers are 250 mm for Examples 1 to 3 and Comparative Example 1, and 290 mm for Example 4.

(2) Impression from Use

The sample disposable warmers prepared in Examples and Comparative Example were taken out from the outer pouch and attached to the shoulder for use. The impression from use (wearing condition and wearing comfort) was evaluated.

Table 1 demonstrates that disposable warmers according to embodiments of the present invention (Examples 1 to 4) are satisfactorily stretchable and excel in impression from use (wearing comfort). In contrast, the disposable warmer having no slit in bag members (Comparative Example 1) shows no stretchability and is inferior in wearing comfort.

The disposable warmer according to Example 4 might be broken when pulled by hand strongly and is somewhat insufficient in strength as compared to the disposable warmers according to Examples 1 to 3.

TABLE 1

| | Slits | | | Stretchability of disposable warmer Length of body warmer after deformation (mm) | Impression from use (wearing comfort) |
|---|---|---|---|---|---|
| | Position | Form | | | |
| Example 1 | heater-free portion | porous film alone of bag member (A) | linear | 270 | Very good with sense of fitness (Very good) |
| Example 2 | heater-free portion | bag member (A) (top member) alone | perforated | 260 | Good with sense of fitness (Good) |

TABLE 1-continued

| | Slits | | Stretchability of disposable warmer Length of body warmer after deformation (mm) | Impression from use (wearing comfort) |
|---|---|---|---|---|
| | Position | Form | | |
| Example 3 | heater-free portion | entire warmer in thickness direction (both top member and backing member) | perforated | 260 | Good with sense of fitness (Good) |
| Example 4 | heat-sealed portion | entire warmer in thickness direction (both top member and backing member) | perforated | 297 | Good but somewhat inferior sense of fitness (Fair) |
| Comparative Example 1 | — | — | — | 250 (no deformation) | No sense of fitness and the warmer detaches when the body moves (Poor) |

What is claimed is:

1. A bag member for a disposable warmer, having a bag including a bag member (A) and a bag member (B), the bag members (A) and (B) being heat-sealed with each other to form the bag, the bag member (A) including at least a layered structure with a porous film and a nonwoven fabric layer, and the bag member (B) including at least another layered structure with a stretchable film and another nonwoven fabric layer; the bag member comprising:
 a heat-sealed portion;
 a portion with a heater to be sealed therein; and
 a heater-free portion,
by heat-sealing the bag member (A) and the bag member (B), wherein a slit is arranged only in the porous film constituting the bag member (A) at the heater-free portion.

2. A disposable warmer comprising having:
 a bag including a bag member (A) and a bag member (B), the bag members (A) and (B) being heat-sealed with each other to form the bag, the bag member (A) including at least a layered structure with a porous film and a nonwoven fabric layer, and the bag member (B) including at least another layered structure with a stretchable film and another nonwoven fabric layer;
 a heater;
 a heat-sealed portion where the bag member (A) and the bag member (B) are heat-sealed;
 a portion with the heater sealed therein;
 two or more of the portions with the heaters sealed therein, independently;
 a slit in at least the porous film constituting the bag member (A) of the bag members (A) and (B) in at least one region between the adjacent portions with the heaters sealed therein; and
 a heater-free portion in at least the one region between the adjacent portions with the heaters sealed therein, the heater-free portion being not heat-sealed and including no heater,
 wherein a slit is arranged, of the bag members (A) and (B), only in the porous film constituting the bag member (A) at the heater-free portion.

3. The disposable warmer according to claim 2, wherein, of the bag members (A) and (B), a slit is arranged only in the bag member (A) so as to pierce the bag member (A) in a thickness direction thereof.

4. The disposable warmer according to claim 3, wherein the stretchable film of the bag member (B) is comprised of a thermoplastic elastomer.

5. The disposable warmer according to claim 3, wherein the nonwoven fabric layers of the bag member (A) and bag member (B) each are independently comprised of a spunlace nonwoven fabric.

6. The disposable warmer according to claim 2, wherein a slit is arranged in the heat-sealed portion so as to pierce the bag member (A) and the bag member (B) in a thickness direction thereof.

7. The disposable warmer according to claim 6, wherein the stretchable film of the bag member (B) is comprised of a thermoplastic elastomer.

8. The disposable warmer according to claim 6, wherein the nonwoven fabric layers of the bag member (A) and bag member (B) each are independently comprised of a spunlace nonwoven fabric.

9. The disposable warmer according to claim 2, wherein a slit is arranged in the heater-free portion so as to pierce the bag member (A) and the bag member (B) in a thickness direction thereof.

10. The disposable warmer according to claim 9, wherein the stretchable film of the bag member (B) is comprised of a thermoplastic elastomer.

11. The disposable warmer according to claim 9, wherein the nonwoven fabric layers of the bag member (A) and bag member (B) each are independently comprised of a spunlace nonwoven fabric.

12. The disposable warmer according to claim 2, wherein the stretchable film of the bag member (B) is comprised of a thermoplastic elastomer.

13. The disposable warmer according to claim 12, wherein the nonwoven fabric layers of the bag member (A) and bag member (B) each are independently comprised of a spunlace nonwoven fabric.

14. The disposable warmer according to claim 2, wherein the nonwoven fabric layers of the bag member (A) and bag member (B) each are independently comprised of a spunlace nonwoven fabric.

* * * * *